US012622628B2

(12) United States Patent
Morrow

(10) Patent No.: US 12,622,628 B2
(45) Date of Patent: May 12, 2026

(54) ELECTRODE FOR ATTENTION TRAINING TECHNIQUES

(71) Applicant: Lana Morrow, New York, NY (US)

(72) Inventor: Lana Morrow, New York, NY (US)

( * ) Notice: Subject to any disclaimer, the term of this patent is extended or adjusted under 35 U.S.C. 154(b) by 0 days.

(21) Appl. No.: 17/852,491

(22) Filed: Jun. 29, 2022

(65) Prior Publication Data

US 2022/0338787 A1     Oct. 27, 2022

Related U.S. Application Data

(63) Continuation of application No. 16/865,515, filed on May 4, 2020, now Pat. No. 11,375,943, which is a continuation of application No. 14/626,403, filed on Feb. 19, 2015, now Pat. No. 10,646,132, which is a continuation of application No. 13/980,759, filed as application No. PCT/US2011/021983 on Jan. 21, 2011, now abandoned.

(51) Int. Cl.
| | |
|---|---|
| *A61B 5/375* | (2021.01) |
| *A61B 5/00* | (2006.01) |
| *A61B 5/291* | (2021.01) |
| *A61B 5/374* | (2021.01) |
| *C22C 9/00* | (2006.01) |
| *G09B 19/00* | (2006.01) |

(52) U.S. Cl.
CPC .............. *A61B 5/375* (2021.01); *A61B 5/291* (2021.01); *A61B 5/374* (2021.01); *A61B 5/6814* (2013.01); *C22C 9/00* (2013.01); *G09B 19/00* (2013.01); *A61B 5/0006* (2013.01); *A61B 5/6831* (2013.01)

(58) Field of Classification Search
CPC ......... A61B 5/375; A61B 5/291; A61B 5/374; A61B 5/6814; A61B 5/0006; A61B 5/6831; C22C 9/00; G09B 19/00
See application file for complete search history.

(56) References Cited

U.S. PATENT DOCUMENTS

| | | | | | |
|---|---|---|---|---|---|
| 4,928,704 | A | * | 5/1990 | Hardt ..................... | A61B 5/375 |
| | | | | | 600/545 |
| 5,038,782 | A | * | 8/1991 | Gevins ................. | A61B 5/0017 |
| | | | | | 600/383 |
| 5,211,174 | A | * | 5/1993 | Imran .................. | A61N 1/0456 |
| | | | | | 252/500 |
| 5,724,987 | A | * | 3/1998 | Gevins ................. | A61B 5/7264 |
| | | | | | 434/258 |

(Continued)

*Primary Examiner* — Jack Yip

(57) ABSTRACT

An electrode includes a core of beryllium copper alloy and a safe metal coating. In some embodiments, the beryllium copper alloy comprises more than three percent beryllium, less than three percent other metals and a remaining percent copper. In some embodiments, an apparatus includes a headband, and a first and second safe metal coated copper-beryllium alloy electrode. The headband is configured to fit snugly to a head of a subject in an orientation from behind a first ear, across a crown of the subject, to a position behind a second ear. The first electrode and second electrode are disposed in the headband to contact a head of the subject at a first position and a different second position, respectively, without gels. In various embodiments, the headband includes a chip to determine an analog signal and transmit data; and, a system includes the headband and a signal analyzing unit.

20 Claims, 10 Drawing Sheets

HEADSET 110

SUBJECT 190

ANALYZER 120

USER INTERFACE 132

INTERFACE SERVER 134

105 COMMUNICATIONS NETWORK

WEB SERVER 142

WEB CLIENT 144

130

140

100

(56)　　　　　　References Cited

U.S. PATENT DOCUMENTS

| | | | | |
|---|---|---|---|---|
| 6,434,419 | B1 * | 8/2002 | Gevins ................... | G16H 50/20 |
| | | | | 600/544 |
| 2002/0122913 | A1 * | 9/2002 | Nee ........................ | G11B 7/259 |
| | | | | 428/64.4 |
| 2004/0193068 | A1 * | 9/2004 | Burton ................. | A61B 5/4812 |
| | | | | 600/595 |
| 2007/0032737 | A1 * | 2/2007 | Causevic ............. | A61B 5/7264 |
| | | | | 128/898 |
| 2007/0225585 | A1 * | 9/2007 | Washbon ............... | A61B 5/291 |
| | | | | 600/383 |
| 2008/0157235 | A1 * | 7/2008 | Rogers ............... | H01L 29/0657 |
| | | | | 257/415 |
| 2010/0041962 | A1 * | 2/2010 | Causevic ................. | A61B 5/38 |
| | | | | 600/383 |
| 2010/0274152 | A1 * | 10/2010 | McPeck ............... | A61B 5/6814 |
| | | | | 600/383 |

* cited by examiner

FIG. 3

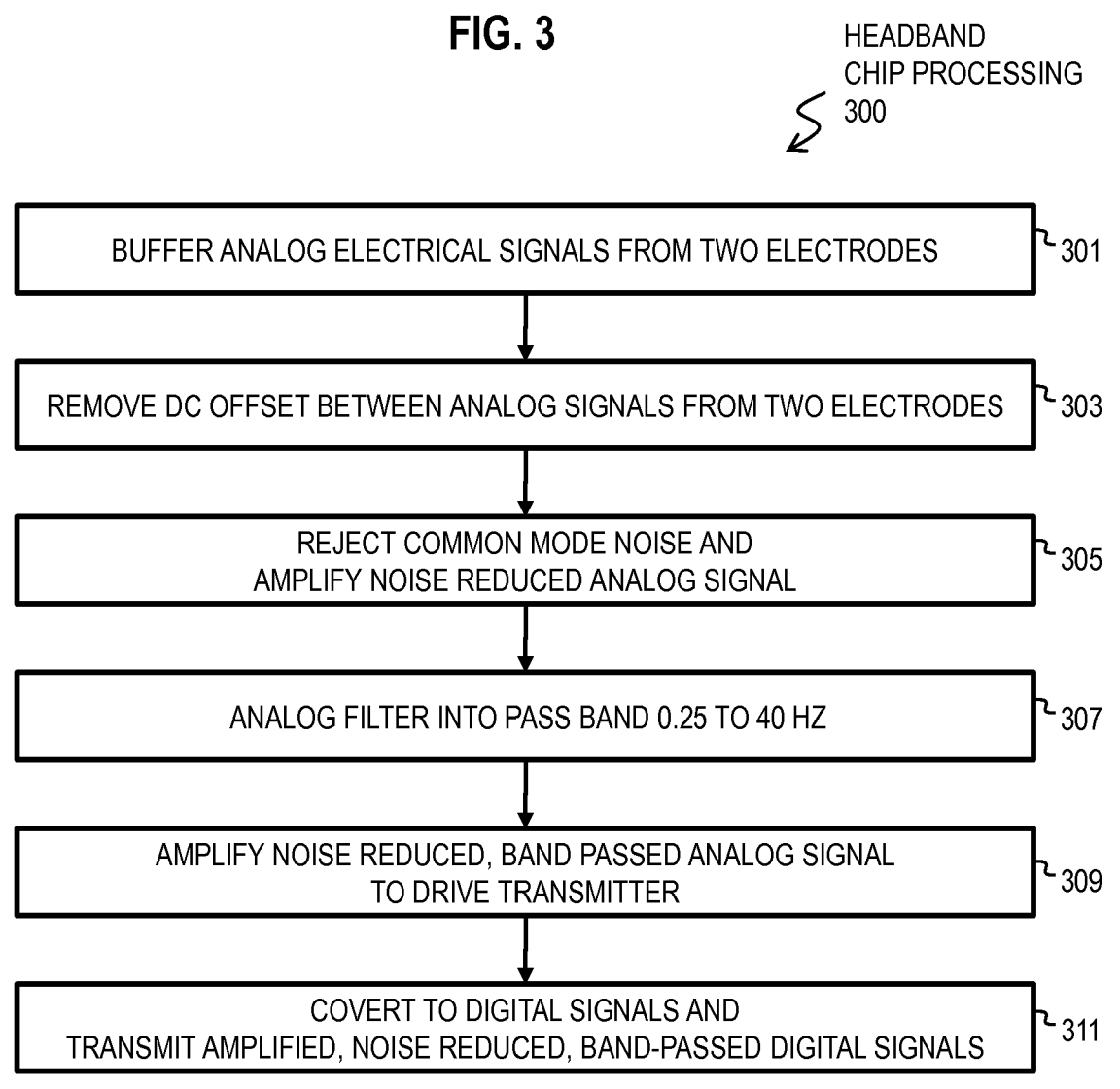

HEADBAND
CHIP PROCESSING
300

| | |
|---|---|
| BUFFER ANALOG ELECTRICAL SIGNALS FROM TWO ELECTRODES | 301 |
| REMOVE DC OFFSET BETWEEN ANALOG SIGNALS FROM TWO ELECTRODES | 303 |
| REJECT COMMON MODE NOISE AND AMPLIFY NOISE REDUCED ANALOG SIGNAL | 305 |
| ANALOG FILTER INTO PASS BAND 0.25 TO 40 HZ | 307 |
| AMPLIFY NOISE REDUCED, BAND PASSED ANALOG SIGNAL TO DRIVE TRANSMITTER | 309 |
| COVERT TO DIGITAL SIGNALS AND TRANSMIT AMPLIFIED, NOISE REDUCED, BAND-PASSED DIGITAL SIGNALS | 311 |

FIG. 4

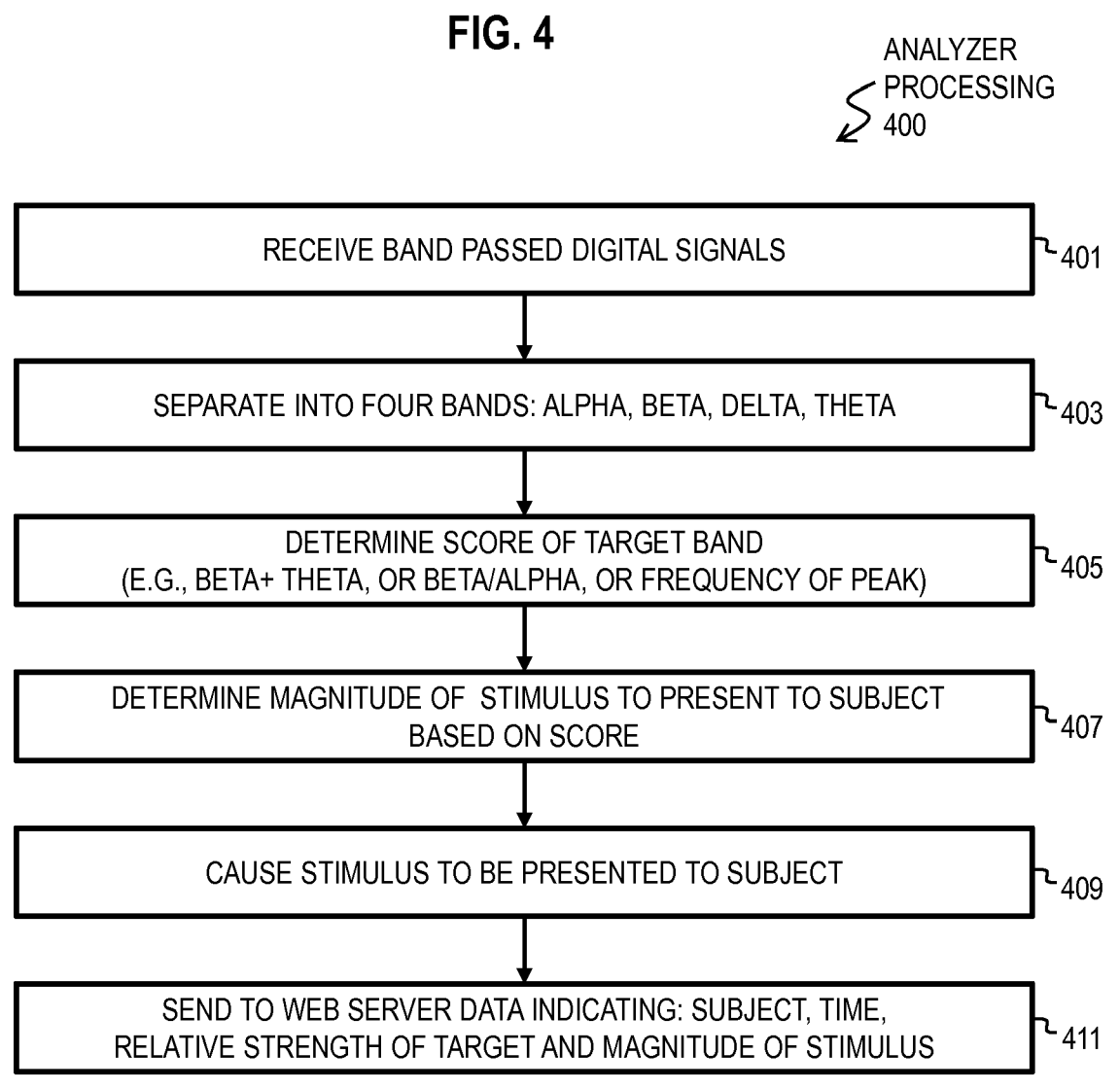

ANALYZER
PROCESSING
400

| RECEIVE BAND PASSED DIGITAL SIGNALS | 401 |

↓

| SEPARATE INTO FOUR BANDS: ALPHA, BETA, DELTA, THETA | 403 |

↓

| DETERMINE SCORE OF TARGET BAND
(E.G., BETA+ THETA, OR BETA/ALPHA, OR FREQUENCY OF PEAK) | 405 |

↓

| DETERMINE MAGNITUDE OF STIMULUS TO PRESENT TO SUBJECT
BASED ON SCORE | 407 |

↓

| CAUSE STIMULUS TO BE PRESENTED TO SUBJECT | 409 |

↓

| SEND TO WEB SERVER DATA INDICATING: SUBJECT, TIME,
RELATIVE STRENGTH OF TARGET AND MAGNITUDE OF STIMULUS | 411 |

FIG. 5

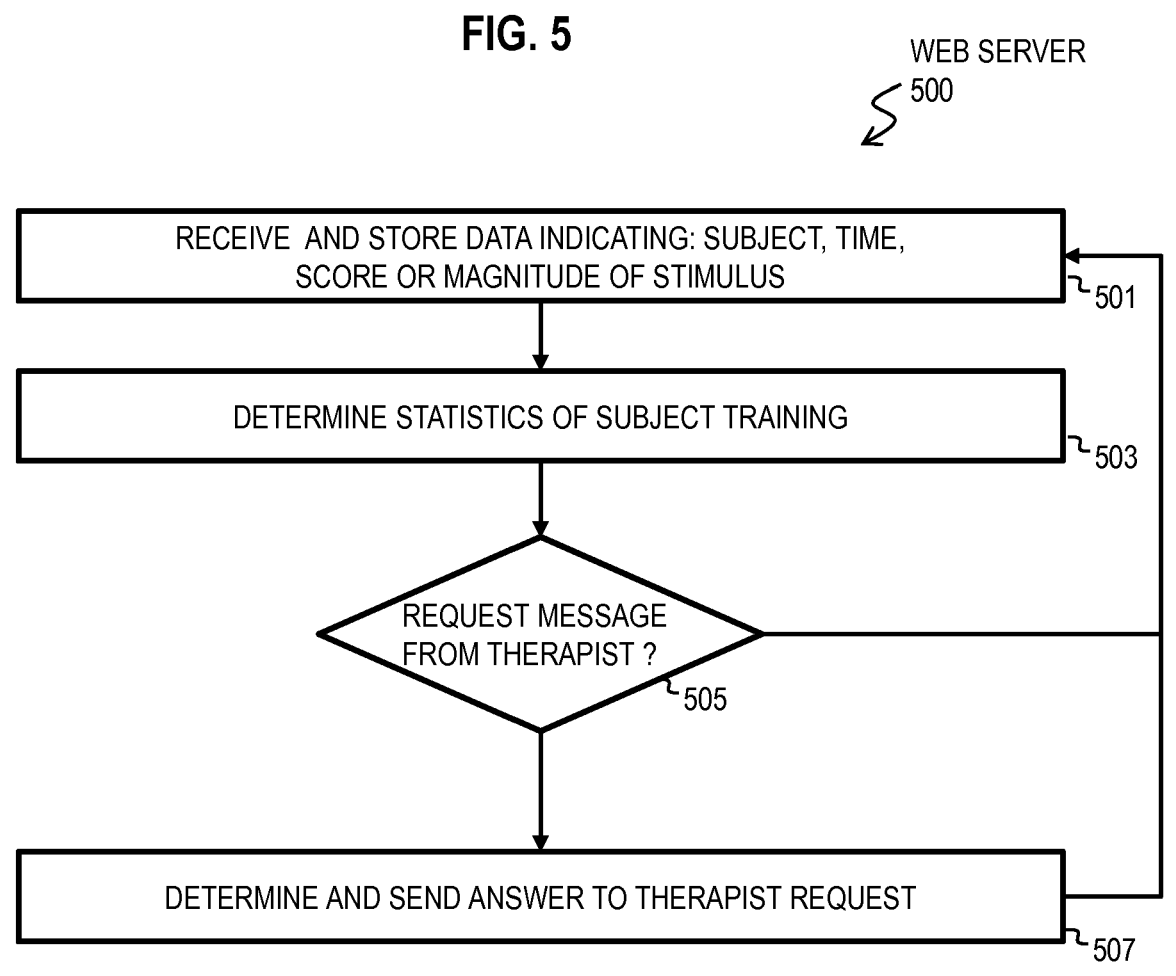

WEB SERVER

500

RECEIVE AND STORE DATA INDICATING: SUBJECT, TIME, SCORE OR MAGNITUDE OF STIMULUS

501

DETERMINE STATISTICS OF SUBJECT TRAINING

503

REQUEST MESSAGE FROM THERAPIST ?

505

DETERMINE AND SEND ANSWER TO THERAPIST REQUEST

507

ELECTRODE FOR ATTENTION TRAINING TECHNIQUES

CROSS-REFERENCE TO RELATED APPLICATIONS

This application is a continuation of U.S. application of Ser. No. 16/865,515, filed May 4, 2020, which is a continuation of U.S. application of Ser. No. 14/626,403, filed Feb. 19, 2015, which is a continuation application of U.S. application Ser. No. 13/980,759 filed on Oct. 7, 2013, which is a national phase filing under 35 U.S.C. 371 of International Application No. PCT/US2011/021983, filed Jan. 21, 2011, and all of these applications are incorporated herein by reference in their entireties.

BACKGROUND

Cognitive learning and operant condition training efficacy to help a person exercise their focusing and working memory skills is well established and leads to long-term increase in attention and memory. This kind of skill learning is equally effective as pharmacotherapy. For example, a news report states, "One interesting treatment is a form of therapy in which children wear electrodes on their head and learn to control video games by exercising the parts of the brain related to attention and focus. Research has suggested that the method works just as well as medication, and many children report that they enjoy it." New York Times, Jun. 20, 2008. Proven permanent benefits of such learning include greater focus, increased working memory and intelligence quotient (IQ), and reduced anxiety.

Unfortunately, many devices for placing electrodes on a subject's head suffer from one or more deficiencies. Deficiencies include, large and bulky head gear, messy liquids or gels or painful scalp abrasions or time consuming processes to place electrodes in good electrical conductance with the subject's scalp, constraining hardwired connections to recording and analyzing equipment, limited stimulus feedback to the subject, and on site presence of a treatment specialist, such as a technician or therapist.

SOME EXAMPLE EMBODIMENTS

Therefore, there is a need for electrodes to be used in attention training, which do not suffer one or more of these deficiencies. For example, there is a need for a lightweight, mobile, wireless headgear with small sensitive electrodes that do not require gels, liquids or abrasions for good electrical contact. Similarly, there is a need for materials that provide good electrical contact with a human head to use in the fabrication of such sensitive electrodes.

According to one set of embodiments, a beryllium copper alloy for such electrodes includes more than three percent by weight beryllium less than about three percent other metals and a substantively remaining percent by weight copper. The other metals are selected from a group comprising cobalt, nickel, iron, gold, silver and lead.

According to another set of embodiments, an electrode for detecting electroencephalogram potentials includes a core of beryllium copper alloy and a coating of safe metal, such as copper or silver.

According to another set of embodiments, an apparatus includes a headband, a first electrode and a second electrode. The headband is configured to fit snugly to a head of a subject in an orientation from behind a first ear of the subject, across a top of a crown of the subject, to a position behind a second ear of the subject. The first electrode comprises a safe metal coated copper-beryllium alloy electrode disposed in the headband to contact a head of the subject at a first position. The second electrode comprises a safe metal coated copper-beryllium alloy electrode disposed in the headband to contact the head of the subject at a different second position.

In some of these embodiments, the apparatus further includes a chip set disposed on the headband. The chip set is configured to determine an analog signal based on a first signal received from the first electrode and a second signal received from the second electrode. The chip set is configured further to transmit, wirelessly, data that indicates the analog signal.

In another set of embodiments, a system includes the apparatus described above and a signal analyzing unit. The signal analyzing unit includes at least one processor and at least one memory including computer program code for one or more programs. The at least one memory and the computer program code are configured to, with the at least one processor, cause the signal analyzing unit to at least receive wirelessly the data that indicates the analog signal and determine, based on the data, at least a first frequency band and a different second frequency band selected from a group comprising an alpha brain wave band, a beta brain wave band, a delta brain wave band and a theta brain wave band. The analyzing unit is further configured to determine a score based on a strength or peak frequency of the first frequency band and a strength or peak frequency of the second frequency band. The analyzing unit is also configured to cause a stimulus to be presented to the subject based at least in part on the score.

According to another set of embodiments, a method includes determining a first electroencephalogram potential temporal trace at an active electrode in contact with a first position on a subject. The method also includes determining a second electroencephalogram potential temporal trace at a reference electrode in contact with a different second position on the subject. Each of the active electrode and reference electrode comprises a safe metal coated copper-beryllium alloy core, and each of the active electrode and reference electrode is disposed in a corresponding position on a headband. The method further comprises determining, in a chip set disposed in the headband, an analog signal temporal trace based on the first electroencephalogram potential temporal trace and the second electroencephalogram potential temporal trace. The method further includes transmitting, from the chip set disposed in the headband, data that indicates the analog signal temporal trace.

In another set of embodiments, a method includes receiving, wirelessly, data that indicates an analog signal temporal trace based on a first electroencephalogram potential temporal trace of a subject and a different second electroencephalogram potential temporal trace of the subject. The method also includes determining, based on the data, at least a first frequency band and a different second frequency band selected from a group comprising an alpha brain wave band, a beta brain wave band, a delta brain wave band and a theta brain wave band. The method further comprises determining a score based on a strength or peak frequency of the first frequency band and a strength or peak frequency of the second frequency ban, and causing a stimulus to be presented to the subject based at least in part on the score.

According to another embodiment, a computer-readable storage medium carries one or more sequences of one or more instructions which, when executed by one or more processors, cause, at least in part, an apparatus to perform one or more steps of one of the above methods.

According to another embodiment, an apparatus comprises means for performing the steps of one of the above methods.

In various example embodiments, the methods (or processes) can be accomplished on a service provider side or on a mobile device side or in any shared way between service provider and mobile device with actions being performed on both sides.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The embodiments of the invention are illustrated by way of example, and not by way of limitation, in the figures of the accompanying drawings:

FIG. 3 is a flowchart that Illustrates an example process for the chip set of FIG. 2C, according to one embodiment;

FIG. 4 is a flowchart that illustrates an example process for the analyzing unit of FIG. 1A, according to one embodiment;

FIG. 5 is a flowchart that illustrates an example process for the web server of FIG. 1A, according to one embodiment;

DESCRIPTION OF SOME EMBODIMENTS

Examples of an alloy, electrode, method, apparatus, and computer program are disclosed for attention training. In the following description, for the purposes of explanation, numerous specific details are set forth in order to provide a thorough understanding of the embodiments of the invention. It is apparent, however, to one skilled in the art that the embodiments of the invention may be practiced without these specific details or with an equivalent arrangement. In other instances, well-known structures and devices are shown in block diagram form in order to avoid unnecessarily obscuring the embodiments of the invention.

Although various embodiments are described with respect to attention training using beta brain waves, it is contemplated that, in other embodiments, the techniques described herein may be used with other training or non-training applications based on any electroencephalography (EEG) signals or other signals detected non-inversely on human skin. In some embodiments, the alloy described herein is used in electrodes for any purpose.

Figure 1A:
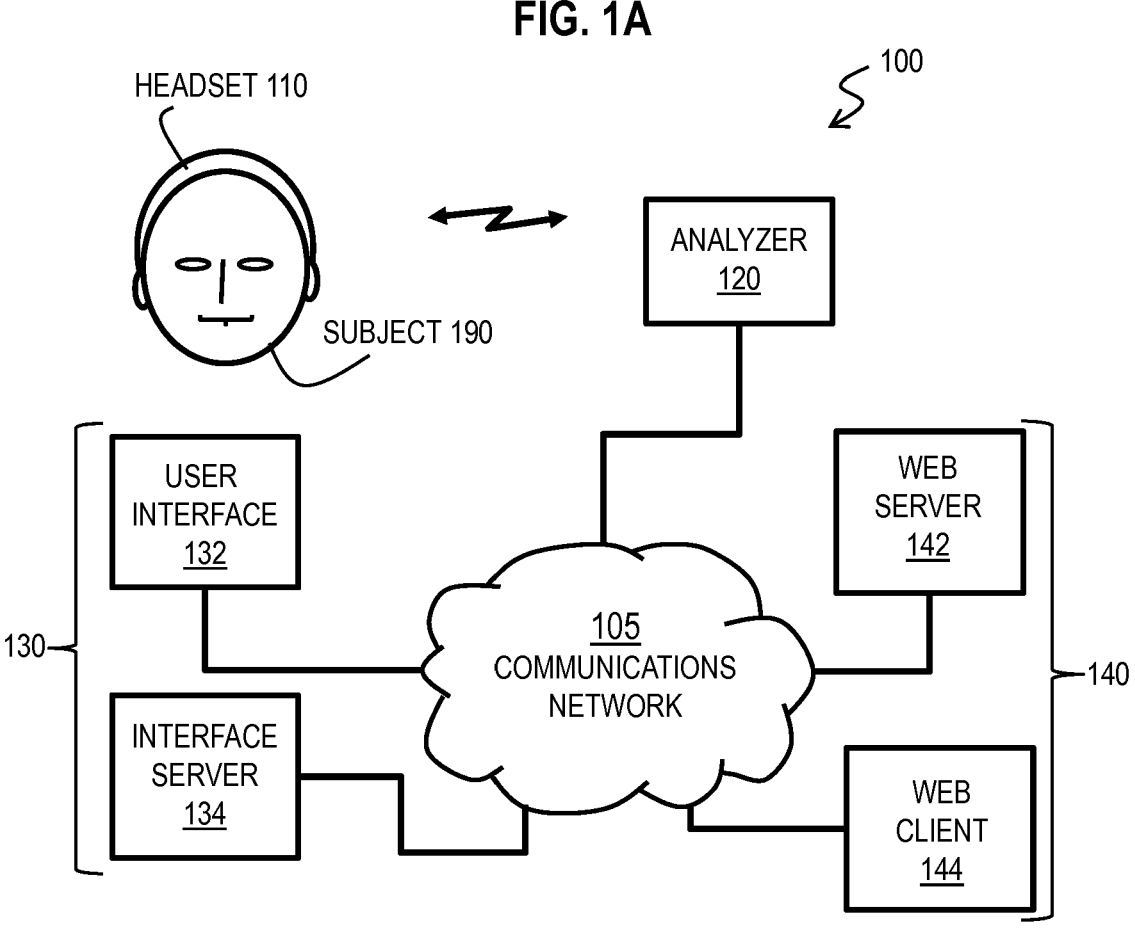
FIG. 1A is a block diagram that illustrates an example system capable of attention training with improved electrodes, according to one embodiment.

FIG. 1A is a block diagram that illustrates an example system 100 cap-able of attention training with improved electrodes, according to one embodiment. This system reduces or eliminates one or more deficiencies of prior approaches, such as large and bulky head gear, messy liquids or gels or painful scalp abrasions or time consuming processes to place electrodes in good electrical conductance with the subject's scalp, constraining hardwired connections to recording and analyzing equipment, limited stimulus feedback to the subject, and on site presence of a treatment specialist, such as a technician or therapist.

To address this problem, the system 100 of FIG. 1A introduces the capability to collect EEG signals from a subject 190 on a lightweight mobile headset 110 that communicates wirelessly with a nearby analyzing unit, called an analyzer 120 for convenience. The analyzer 120 is in communication with one or more other network devices via communications network 105. This allows a stimulus to be presented to the subject 190 at a user interface module 132 as determined by an interface server module 134 based on data sent from the analyzer 120. In some embodiments, data produced by the analyzer 120 is stored on a web server module 142 where it can be accessed by the interface server 134. Furthermore the data at web server 142, in some embodiments, are accessed by a web client module 144 (such as a browser) for the benefit of one or more remote users, such as a technician or therapist. Although a head of subject 190 is depicted for the purposes of illustration, the subject 190 is not part of the system 100.

As shown in FIG. 1A, the system 100 comprises a headset 110 and an analyzer 120 and user interface 132 and web client 144 having connectivity to web server 142 or interface server 134, or some combination, via a communication network 105. By way of example, the communication network 105 of system 100 includes one or more networks such as a data network (not shown), a wireless network (not shown), a telephony network (not shown), or any combination thereof, it is contemplated that the data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

The analyzer 120 and user interface module 132 is any type of mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, or any combination thereof, including the accessories and peripherals of these devices, or any combination thereof. It is also contemplated that the analyzer 120 and user interface 132 can support any type of interface to the user (such as "wearable" circuitry, etc.), including the mobile headset 110.

Scalp recordings of neuronal activity in the brain, identified as an EEG, allow measurement of potential changes over time in basic electric circuit conducting between signal (active) electrode and reference electrode. Extra third electrode, called ground electrode, is sometimes used. Differential voltages are obtained by subtracting the same voltages showing at active and reference points. A minimal configuration for mono-channel EEG measurement is considered to consist of one active electrode, one (or two specially linked together) reference electrode(s) and one ground electrode. Multi-channel configurations can comprise up to 128 or 256 active electrodes. In 1958, International Federation in Electroencephalography and Clinical Neurophysiology adopted a standard for electrode placement called 10-20 electrode placement system. This system standardized physical placement and designations of electrodes on the scalp. The head is divided into proportional distances from prominent skull landmarks (nasion, pre-auricular points, inion) to provide adequate coverage of all regions of the brain. Labels for the 10-20 electrode placement system designates proportional distance in percents between ears and nose where points for electrodes are chosen. Electrode placements are labeled according adjacent brain areas: F (frontal), C (central), T (temporal), P (posterior), and 0 (occipital). The letters are accompanied by odd numbers at the left side of the head and with even numbers on the right side. Left and right side is considered by convention from point of view of a subject.

Figure 1B:
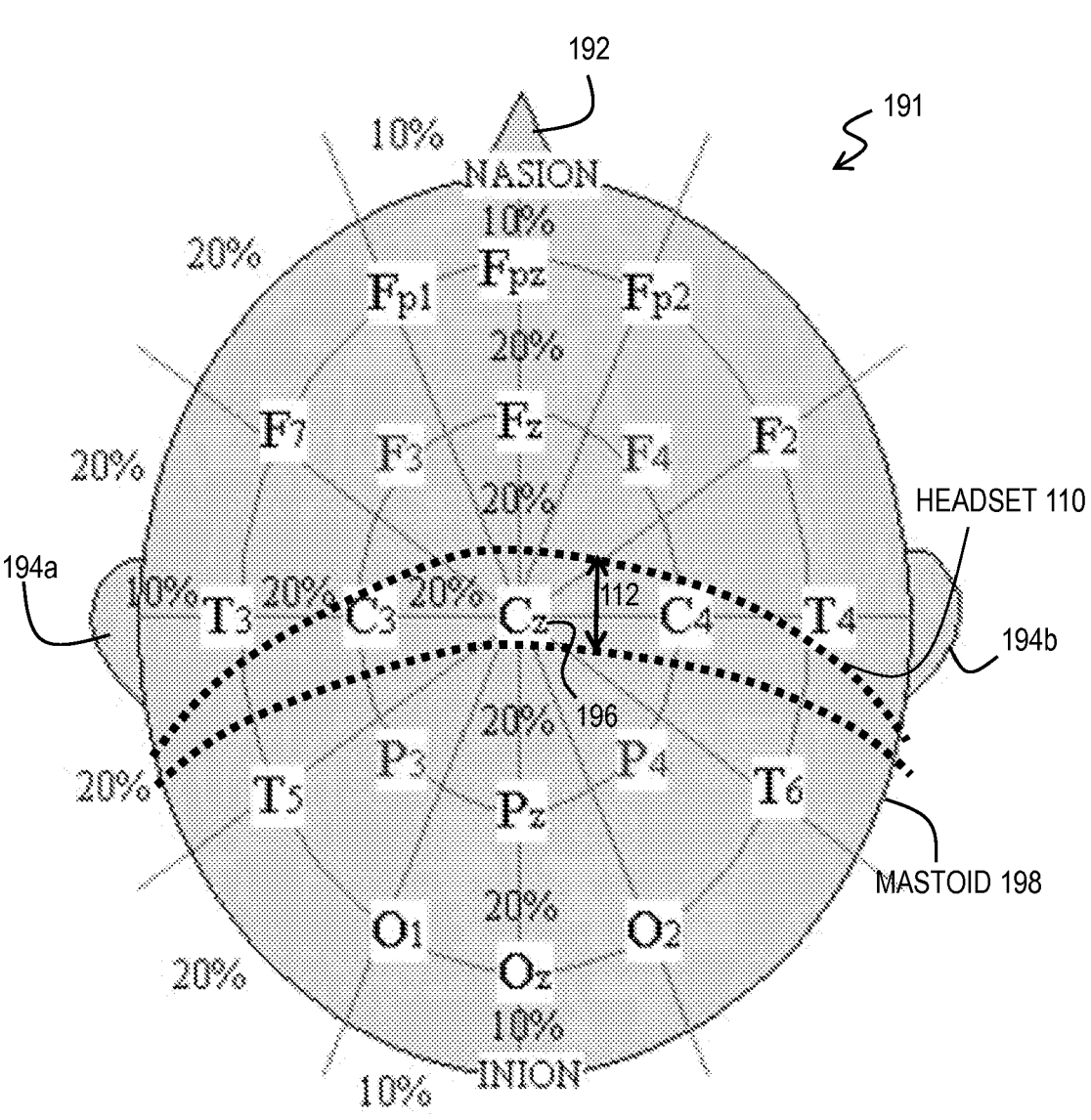
FIG. 1B is a diagram that illustrates example placement of a headset relative to the 10-20 electrode placement system of the International Federation of Electroencephalography and Clinical Neurophysiology, according to an embodiment.

The headset 110 provides lightweight, mobile, fast, easy, robust and sensitive electrical contact with the subjects head, preprocessing and wireless transmission of EEG data. FIG. 1B is a diagram that illustrates example placement of headset 110 relative to the 10-20 electrode placement system 191 of the International Federation of Electroencephalography and Clinical Neurophysiology, according to an embodiment. The subject's head is depicted from above. A nose 192 establishes the "naison" position, and a line between left ear 194 *a* and right ear 194 *b* defines the central brain areas C3, Cz and C4. A mastoid area is located behind each ear at the back of a temporal skull plate; mastoid area 198 behind right ear 194 *b* is depicted in FIG. 1B. A headband component of the headset 110 is configured to fit snugly to a head of a subject in an orientation from behind a first ear 194 *a* of the subject, across a top of a crown of the subject, to a position behind a second ear 194 *b* of the subject. In some embodiments, the headband is designed ergonomically to be comfortable to wear for long periods of several hours. In the illustrated embodiment, the headband passes over the Cz position 196 at the top of the crown of the subject. The width

112 of the headband in the vicinity of the Cz position 196 is depicted. In some embodiments, to minimize the bulkiness and weight of the headset, the headband component is limited in size and weight. For example, a width 112 of four centimeters or less is used.

In the illustrated embodiments the components of the headset 110 are described in more detail below with reference to FIGS. 2A through 2C. In some embodiments, the headset includes some processing of EEG signals, including noise reduction, filtering, and determining a differential signal. The processing is described in more detail below with reference to FIG. 3.

Referring again to FIG. 1A, the analyzer 120 is placed within transmission range of the headset 110, to receive from the headset 110 the data that describes EEG signals in one or more frequency bands. As described in more detail below with reference to FIG. 4. The analyzer 120 determines signal strength in one or more brain wave bands and determines a score to be used to reward or penalize a subject 190 based on absolute or relative signal strength in two or more brain wave bands. Standard brain wave frequency bands are typically defined as follows, in order of increasing frequency in hertz (Hz, 1 Hz=1 cycle per second):

delta brain wave band (0.5-4 Hz);
theta brain wave band (4-8 Hz);
alpha brain wave band (8-13 Hz);
beta brain wave band (>13 Hz).

Brain patterns form wave shapes that are commonly sinusoidal; are measured from peak to peak; and normally range from 0.5 to 100 micro volts ($\mu V$, 1 $\mu V=10^{-6}$ volts, V) in amplitude, which is about 100 times lower than electrical signals measured at the surface of the skin in the vicinity of the heart. The processing by the analyzer 120 is described in more detail below with reference to FIG. 4.

The score provided by the analyzer 120 can be used for many purposes, including controlling games or biofeedback or other applications. In some embodiments, the subject 190 is provided a stimulus at a user interface module 132 based on the score. In some embodiments, an interface server module 134, such as a game controller, obtains the score from the analyzer 120 and uses the score to determine a stimulus to present on the user interface module 132, such as a video screen, television, speakers, or tactile presentation device. Thus, in some embodiments, analyzer 120 acts as universal game adaptor that teaches the user to exercise his or her powers of attention and memory skills through a series of entertaining video games on one or more modules 134. In some embodiments, analyzer 120 acts as universal adaptor that teaches the user to exercise his or her powers of attention and memory skills through existing cognitive tools on one or more modules 134. In some embodiments, the wireless interface between headset 110 and analyzer 120 can use a game wireless protocol, and thus be used as an add-on to existing wireless games to add benefit of playing. Some or all functions of the analyzer are thus incorporated in the interface server 134, in such embodiments. An advantage of such an embodiment is to allow game designers to determine theft own score to help a person exercise her or his attention and focusing or different mental skills, like relaxing, while playing games that exist on the market. Together, the interface server 134 and user interface 132 constitute a subject stimulation system 130.

In some embodiments, a remote user (e.g., technician or care giver, such as a therapist), has access to some or all of the data determined by the analyzer 120. For example, the data is stored in a secure database at web server 142, and a remote user accesses the web server 142 through a web client 144, such as a World Wide Web browser (described below). The server 142 may send a challenge, such as a password request, to the client 144, which, if successfully met, authorizes a user of client 144 to access the information about subject 190 in the database of web server 142. Together, the web server 142 and web client 144 constitute a remote user system 140. Thus, in some embodiments, a therapist user of web client 144 can assess the progress or lack thereof for subject 190.

Although components are depicted as several integral modules in a particular arrangement in FIG. 1A, in other embodiments, one or more modules or portions thereof are combined in a different arrangement in one or more hosts or devices connected to network 105. It is contemplated that the functions of these components may be combined in one or more components or performed by other components of equivalent functionality. For example, in some embodiments, the interface server module 134 and user interface module 132 are processes in a single user interface device, such as a game console or cell phone (or other mobile terminal) or personal computer. In some embodiments of another example, described above, the headset 110 communicates directly with the interface server 134, which includes one or more functions of the analyzer 120.

By way of example, the headset 110 and analyzer 120 communicate with each other and other components of the communication network 105 (such as subject stimulation system 130 or remote user system 140, or some combination) using well known, new or still developing protocols. In this context, a protocol includes a set of rules defining how the network nodes within the communication network 105 interact with each other based on information sent over the communication links. The protocols are effective at different layers of operation within each node, from generating and receiving physical signals of various types, to selecting a link for transferring those signals, to the format of information indicated by those signals, to identifying which software application executing on a computer system sends or receives the information. The conceptually different layers of protocols for exchanging information over a network are described in the Open Systems Interconnection (OSI) Reference Model.

Communications between the network nodes are typically effected by exchanging discrete packets of data. Each packet typically comprises (1) header information associated with a particular protocol, and (2) payload information that follows the header information and contains information that may be processed independently of that particular protocol.

Processes executing on various devices, often communicate using the client-server model of network communications, widely known and used. According to the client-server model, a client process sends a message of one or more data packets including a request to a server process, and the server process responds by providing a service. The server process may also return a message of one or more data packets with a response to the client process. Often the client process and server process execute on different computer devices, called hosts, and communicate via a network using one or more protocols for network communications. The term "server" is conventionally used to refer to the process that provides the service, or the host on which the process operates. Similarly, the term "client" is conventionally used to refer to the process that makes the request, or the host on which the process operates. As used herein, the terms "client" and "server" and "service" refer to the processes, rather than the hosts, unless otherwise clear from the context. In addition, the process performed by a server can be broken up to run as multiple processes on multiple hosts (sometimes called tiers) for reasons that include reliability, scalability, and redundancy, among others. A well known client process available on most devices (called nodes) connected to a communications network is a World Wide Web client (called a "web browser," or simply "browser") that interacts through messages formatted according to the hypertext transfer protocol (HTTP) with any of a large number of servers called World Wide Web (WWW) servers that provide web pages.

Figure 2A:
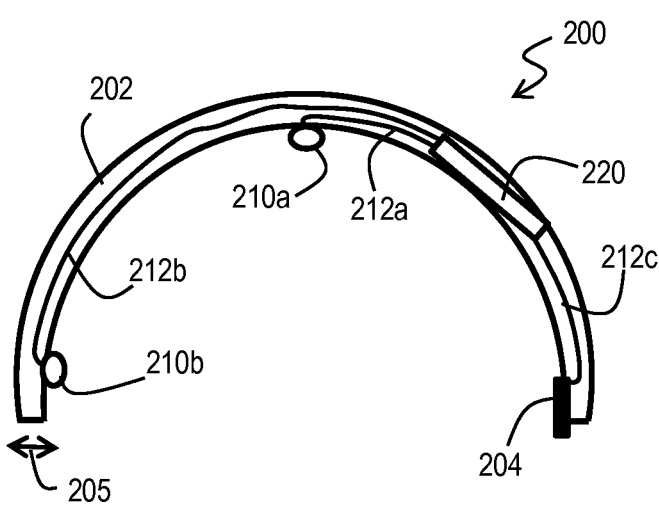
FIG. 2A is a block diagram that illustrates an example head gear apparatus, according to an embodiment.

FIG. 2A is a block diagram that illustrates an example head gear apparatus (called a headset 200 hereinafter), according to an embodiment. The headset 200 is a particular embodiment of headset 110. Headset 200 includes a headband 202 to which is attached one active electrode 210 *a* and one reference electrode 210 *b* (collectively referenced hereinafter as EEG electrodes 210), and corresponding leads 212 *a* and 212 *b*, respectively, connecting the electrodes to a headset chip set 220. The headset chip set 220 is also attached to the headband 202 in the illustrated embodiment. In some embodiments, the headband is made of molded plastic because it is light, rigid and an electrical insulator. In other embodiments a thin metal strip is used with insulated leads and chip set. In some embodiments, the thickness 205 of the headband is about one centimeter thick or less to keep the headset 200 as light as possible, but still strong enough to fit snugly and apply some pressure on the subject's head at the locations of the electrodes 210.

In some embodiments the headset 200 includes one or more additional active or reference electrodes, or both. An advantage of multiple electrodes is a richer variety of signals for noise rejection or determining one or more scores for a subject. An advantage of a single active electrode and a single reference electrode is simplicity, lower cost, and fewer components in the chip set 220 for a smaller, lighter cheaper chip set 220. In some embodiments, the electrodes 210 are beryllium copper electrodes with superior electrical properties that allow a higher signal to noise ratio with fewer electrodes. In some embodiments, a ground electrode 204 is included with a lead 212 *c* to provide electrical ground for chip set 220. Because detection of brain waves is not involved, any electrode may be used as the ground electrode 204, including copper, silver and beryllium copper electrodes.

In the example embodiment, the active electrode 210 *a* is placed in the headband 202 to contact the subject in the vicinity of the Cz point 196; and the reference electrode 210 *b* is placed in the headband 202 to contact the subject in the vicinity of the mastoid point 198. An advantage of this placement is that the brain waves associated with attention are strong near the Cz point 196 and weak near the mastoid 198.

A beryllium copper alloy was developed to provide superior electrical properties compared to other EEG electrodes. In one embodiment, the beryllium copper alloy comprises 4% by weight beryllium, 93.5% copper, 1% an alloy of 50% nickel and 50% cobalt, 0.7% an alloy of one third nickel and one third cobalt and one third, and 0.8% lead.

In other embodiments, an alloy comprises about 3%-6% beryllium; less than about 3% one or more metals selected from a group comprising cobalt, nickel, iron, silver, gold and lead; and a remaining percent copper.

In an example embodiment, the alloy is fabricated by melting copper at 980 to 1030 degrees Celsius (° C.) and adding the other constituents at 1100° C. degrees and stirring for about one half hour, then cooling to an annealing temperature of 700 degrees for 2 hours. After further cooling, the alloy is then washed with water and dried by baking.

Beryllium is often avoided in electrodes configured to contact human skin, because beryllium is considered a carcinogen when in airborne dust, e.g., from grinding. To circumvent this issue, the electrodes 210 are formed with a beryllium copper core and a safe metal coating. As used herein a safe metal is one that is not considered a health hazard when in contact with human skin, such as copper, gold and silver. For example, in some embodiments, a 0.1 millimeter (mm, $1\ mm=10^{-3}$ meters) copper coating is formed on a core of beryllium copper alloy.

Figure 2B:
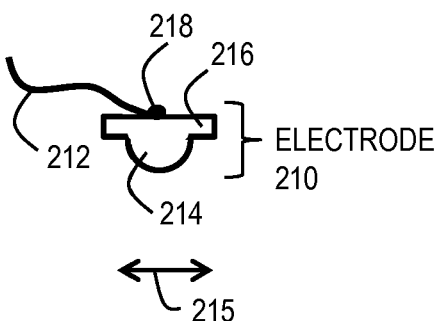
FIG. 2B is a block diagram that illustrates an example electrode for the head gear apparatus, according to an embodiment.

FIG. 2B is a block diagram that illustrates an example electrode 210 for the head gear apparatus 200, according to an embodiment. The electrode includes a safe metal coated base 216 and a safe metal coated core 214, wherein the core is narrower at a tip configured to contact a head of a subject than at a base configured to be attached to head gear. An advantage of the narrower tip is to contact the skin of the scalp even with hair on the scalp. In some embodiments, the core is shaped as a figure of rotation, so that the tip is smooth and does not scour or otherwise irritate the skin of the scalp. In the illustrated embodiment, the core is shaped as a hemisphere; while, in various other embodiments, the core is shaped as a hemispheroid or a smaller portion of a spheroid. A lead wire 212 is connected to the electrode at a connection 218, such as a nut and post or weld joint or solder joint.

To keep the headset 200 as light as possible, the electrode is as small as possible to still make good electrical contact with the skin of the scalp without aid of gels or liquids and without breaking the skin of the subject. For example, in some embodiments, the electrode 210 extends perpendicular to the headband 202 by about three millimeters or less. This is effectively the radius of the spherical safe metal coated core depicted in FIG. 2B. Similarly, in some embodiments, the electrode 210 has a base contact area on the headband, represented by diameter 215, which is about four millimeters or less.

In an experimental embodiment, a headband with a copper coated beryllium copper core electrode was tested. In twenty tests, good EEG signals were obtained with amplitudes indicating electrical impedance at the scalp-electrode interface of about 3 kilo ohms (k$\Omega$, $1\ k\Omega=10^3$ ohms) or less. These good results were attained with subjects moving and talking, and without special scalp preparation, including without removing or washing the subject's hair.

The experimental setup included a subject sitting directly in front of a computer at a distance of about 2 meters (m). The subject had the headband on top of the scalp, and the electrodes were positioned as follows: one electrode was at Cz; the reference electrode was at a mastoid level, just behind the left ear; the ground electrode was diametrically opposite of the reference electrode, i.e. at the level of the mastoid near the right ear. The device placed in the light headband amplified the signal, sending it to a receiver in the computer. The signal was then converted into values and was able to pass with valid signal to noise ratio, which enabled the reception of clear data. Impedances were consistently maintained below 3 kilo ohms. The equipment recorded the EEG activity at a speed of 2032 samples per second in continuous streaming, and the subject was asked to focus on the game before him/her.

Figure 2C:
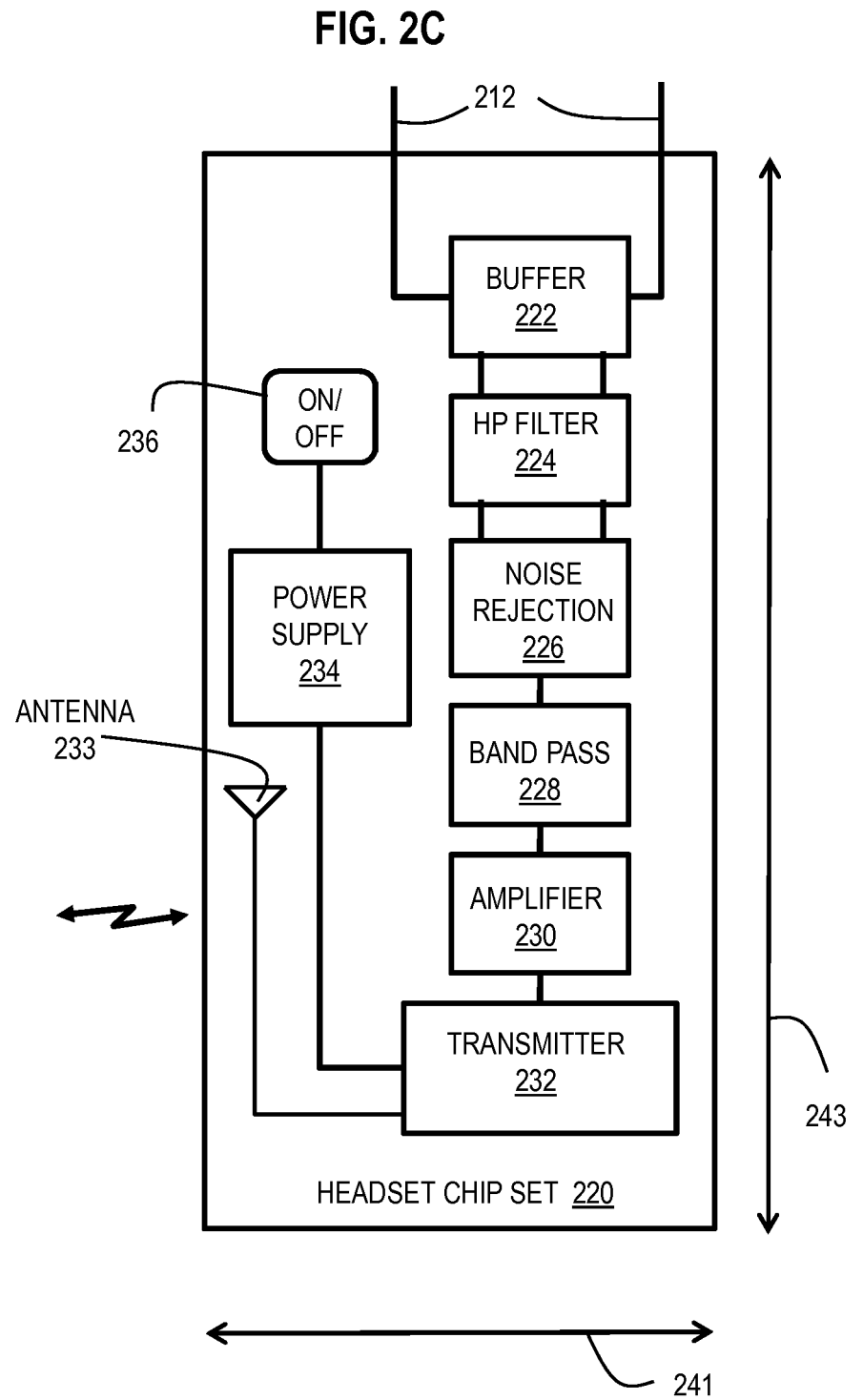
FIG. 2C is a block diagram that illustrates an example chip set for the head gear apparatus, according to an embodiment.

FIG. 2C is a block diagram that illustrates an example chip set 220 for the head gear apparatus 200, according to an embodiment. The chip set 220 performs collection of the analog EEG signals from the electrodes 210, some preprocessing that can be done effectively in small footprint analog components and wireless transmission of data based on the pre-processing to the analyzer unit. To help reduce the size and weight of the headset, short range transmission (a few dozen meters) is used in some embodiments. For example 20 meter range transmission using the BLUETOOTH® protocol is employed in some embodiments.

In an illustrated embodiment, the chip set includes buffer module 222 to match impedance of input on leads 212 connected to electrodes 210, a high pass (HP) filter module 224 to remove a direct current (DC) offset, an noise rejection module 226 to reduce common mode noise, a band pass filter 228 to pass the frequency band of interest, an amplifier to boost the signal for transmission, a transmitter 232 to send data wirelessly to the analyzer 120 through antenna 233, and a power supply 234 with an on/off module 236. In some embodiments, a chassis for chip set 220 is connected to the ground electrode 204, e.g., to prevent drift of electrical output.

In an example embodiment, the buffer module 222 entails impedance matching of about 1 k$\Omega$ on each of two leads 212 from the two safe metal coated beryllium copper electrodes 210. The HP filter module 224 removes a DC offset from each of the two signals (active and reference, respectively) on the two leads. The noise rejection module 226 reduces common mode noise found in both signals, e.g., by differencing the two signals, with or without a relative delay introduced to one of the signals. For example, the module 226 is a differential amplifier that also amplifies the voltage difference between the two signals. This amounts to subtracting the signal on the reference electrode from the signal on the active electrode. The reference electrode reflects all sorts of skin currents, such as currents induced by nearby power circuits, not associated with cerebral cortex activity that predominates the Cz signal on the active electrode. In various embodiments, one or more of the modules 222, 224, 226 operate on analog signals with lithe distortion in the 0.25 to 40 Hz frequency range of brain waves of interest.

The band pass module 228, passes signals with frequencies in at least the beta and theta brain wave bands used in the illustrated embodiment. For example, the module 228 passes frequencies in a frequency band from at least about four (4) Hertz to at least about twenty (20) Hertz, comprising beta brain waves and theta brain waves (and intervening alpha brain waves). Thus, this band also includes the alpha brain wave band but leaves out the delta brain wave band and higher frequency in the beta band that might be affected by power line noise (50 HZ in some countries and 60 Hz in much of the United States). In some embodiments, higher frequencies in the beta brain wave band, or the delta brain wave band, or both are included. For example, the module 228 passes frequencies in a wider frequency band from about one quarter (0.25) Hertz to about forty (40) Hertz, comprising alpha brain waves, additional beta brain waves, delta brain waves and theta brain waves. In various embodiments, the modules 228 operate on analog signals with little distortion in the pass band.

In the amplifier 230, the band passed signal is increased in amplitude sufficiently to drive the transmitter 232 to produce a measurable signal out to a design transmission range, such as 20 to 100 meters, through antenna 233. In some embodiments, an analog signal is sent over transmitter 232 through antenna 233. In some embodiments, the amplifier or transmitter includes an analog to digital converter (ADC), so that digital data can be sent by transmitter 232 through antenna 233. An advantage of sending digital data is a capacity to send several minutes of signals with frequency content up to 40 Hz, in less than a second. This is because a 0.25 Hz to 40 Hz signal is well sampled with 80 samples per second. Assuming each sample involves an octet (eight binary digits called bits), this example involves a sampling rate of 640 bits per second. Common wireless digital transmission rates are highly reliable over 1 Megabits per second (Mbps, 1 Mbps=$10^6$ bits per second), which can send one minute of data (640 bits per second times 60 seconds=38400 bits) in about 4 milliseconds (ms, 1 ms=$10^{-3}$ seconds).

Power for the components 222 through 232 is provided by a power supply module 234. The chip set, and consequently headset 220 is turned on and off using an on/off mechanism 236, such as a button or toggle switch. The power output by power supply 234 is consumed fastest by transmitter 232. The farther the transmission is to be detected, the greater the power consumption used to transmit. In some embodiments, to further help reduce the size and weight of the headset, the transmission range is very short, e.g., about 20 meters, to consume less power and require a smaller, lighter power supply 234 to persist a given mean time between recharging, such as two hours. For example, in some embodiments, the transmitter 232 uses BLUETOOTH protocol technology.

To further help reduce the size and weight of the headset small, light components are used in chip set 220. For example, in some embodiments, one or more conductors or components include nanometer thick graphene, which suffer less dissipation loss, thus reducing heat of the chip set and reducing the drain on power supply 234, as well as providing faster conduction and more reliable operation and smaller and lighter chip sets.

Figure 7:
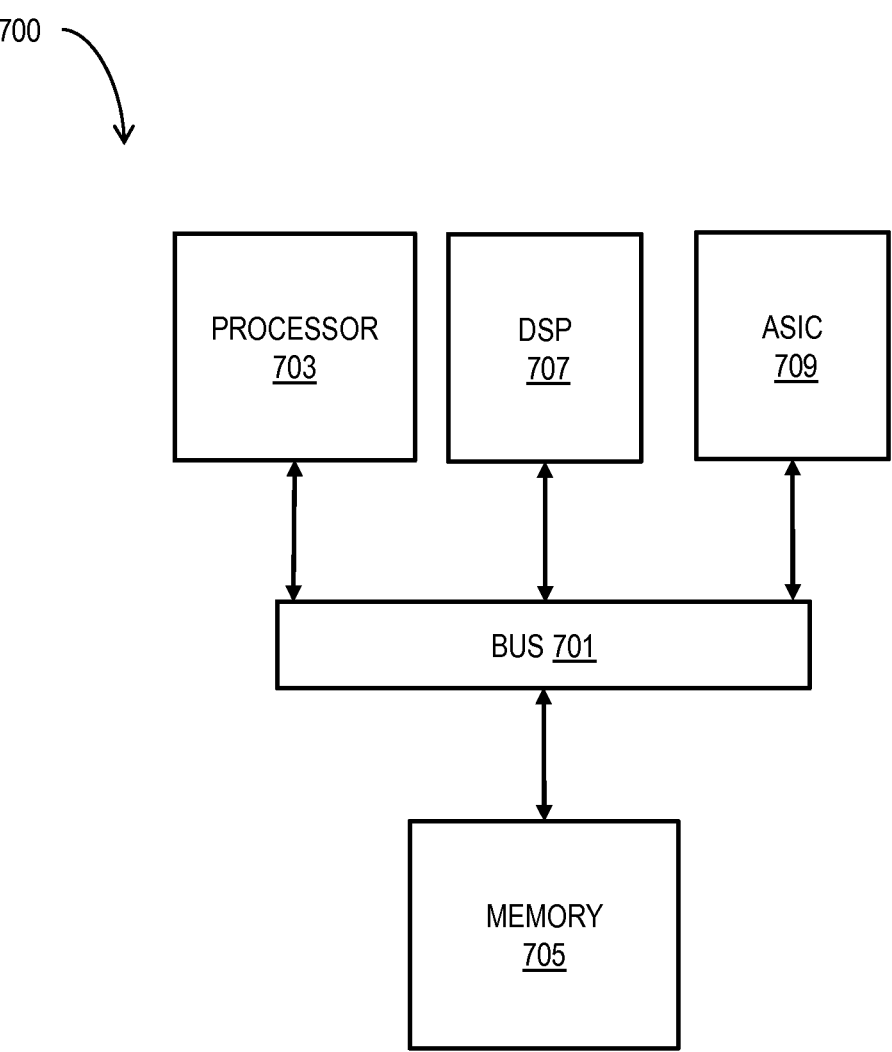
FIG. 7 is a diagram of a chip set that can be used to implement an embodiment of the invention.

FIG. 3 is a flowchart that illustrates an example process for the chip set of FIG. 2C, according to one embodiment. In one embodiment, the chip set 220 performs the process 300 and is implemented in, for instance, a chip set including a processor and a memory as shown in FIG. 7. Although methods are depicted in FIG. 3, and subsequent flow charts in FIG. 4 and FIG. 5, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 301, analog electrical signals from two electrodes are buffered to match impedances to 1 kilo ohm. In step 303, DC offsets are removed from the two analog signals from the two electrodes. In step 305, common mode noise is rejected and the noise-reduced analog signal is amplified, e.g., in a differential amplifier. In step 307 the analog filter is band passed, e.g., passing the 0.25 to 40 Hz frequencies. In some embodiments that use only beta and theta brain waves, the band passed frequency range is about four (4) to about twenty (20) Hz. This removes high frequency noise that would be abased into the digital data in an ADC, if not removed before digitization. This also removes a high energy peak, at 50 or 60 Hz, which would remain in the noise-reduced data due to the strong residual contribution at one of the power line frequencies. In step 309, the noise reduced, band passed analog signal is amplified to drive the transmitter to reach design transmission ranges. In step 311, the amplified analog signal is converted transmitted wirelessly. In some embodiments, the analog signal is converted to digital data during step 311 and transmitted as digital data in a fraction of the time in one or more data packets.

In some embodiments, one or more of steps 303, 305, 307 and 309 is omitted from the chip set 220 and performed at the analyzer 120. In such embodiments, during step 311, analog data for each of the two analog signals is transmitted on a corresponding one of two separate channels, e.g., as frequency modulated or amplitude modulated signals on two different carrier frequencies.

Thus, method 300 includes at least, during step 301, determining a first electroencephalogram potential temporal trace at an active electrode in contact with a first position on a subject and determining a second electroencephalogram potential temporal trace at a reference electrode in contact with a different second position on the subject. In some embodiments, each of the active electrode and reference electrode comprises a safe metal coated copper-beryllium alloy core, and each of the active electrode and reference electrode is disposed in a corresponding position on a headband. Step 301 includes determining, in a chip set disposed in the headband, two analog temporal traces based on the first electroencephalogram potential temporal trace and the second electroencephalogram potential temporal trace. Step 311 includes transmitting, from the chip set disposed in the headband, data that indicates the analog signal temporal trace or traces.

In some embodiments, steps 303, 305, 307 and 309 are included, and step 305 includes determining, in a chip set disposed in the headband, one analog signal temporal trace (e.g., differential amplifier output) based on the first electroencephalogram potential temporal trace and the second electroencephalogram potential temporal trace. In these embodiments, determining the analog signal temporal trace further comprises determining a common mode noise reduced difference between the first electroencephalogram potential temporal trace and the second electroencephalogram potential temporal trace in a frequency band from at least about four (4) Hertz to at least about twenty (20) Hertz, comprising beta brain waves and theta brain waves. If a wider band pass is used in step 307, in some embodiments, then the analog signal temporal trace indicates a common mode noise reduced difference between the first electroencephalogram potential temporal trace and the second electroencephalogram potential temporal trace in a frequency band from about one quarter (0.25) Hertz to at least about forty (40) Hertz, comprising alpha brain waves, beta brain waves, delta brain waves and theta brain waves.

Figure 6:
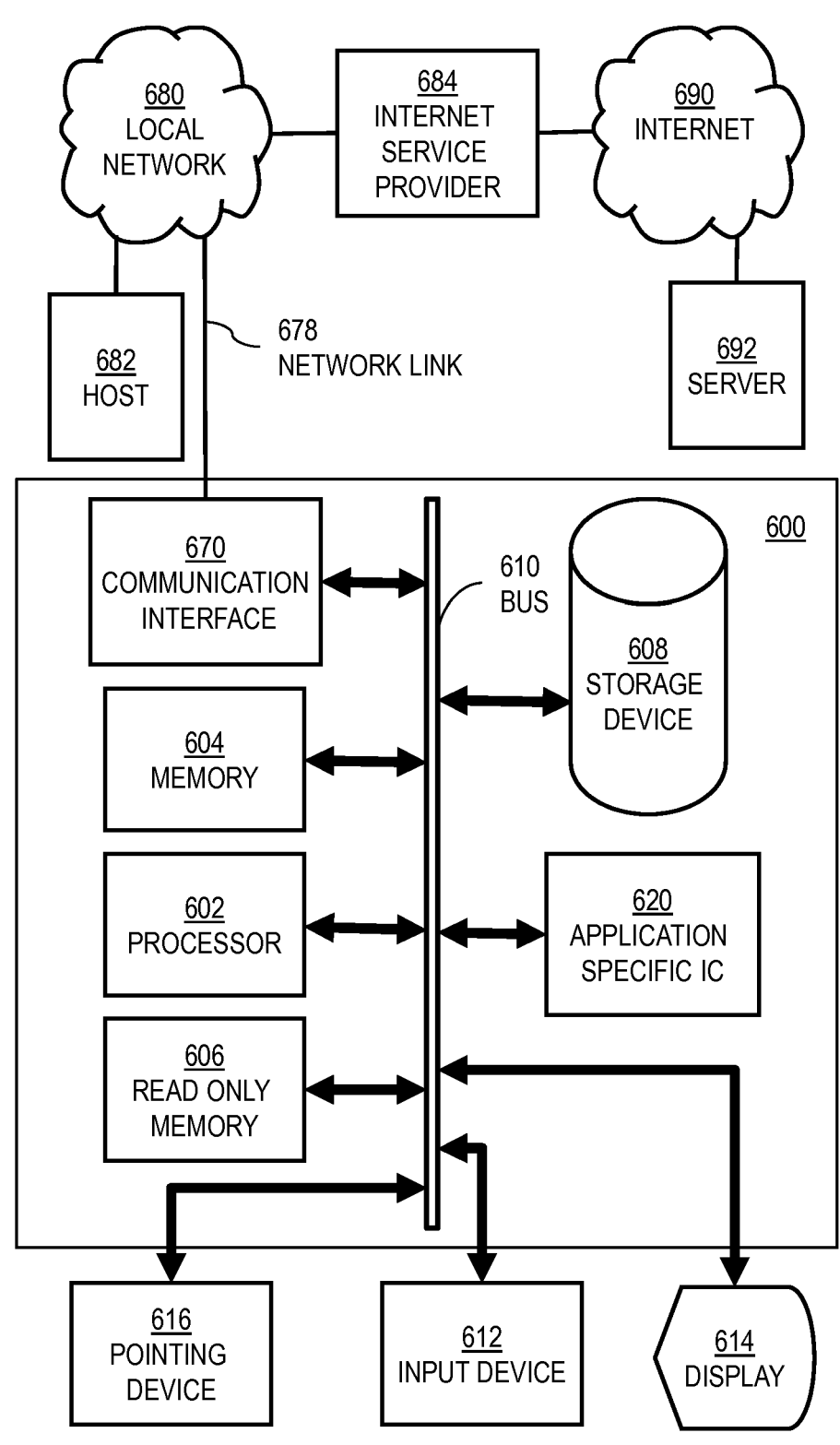
FIG. 6 is a diagram of hardware that can be used to implement an embodiment of the invention.
Figure 8:
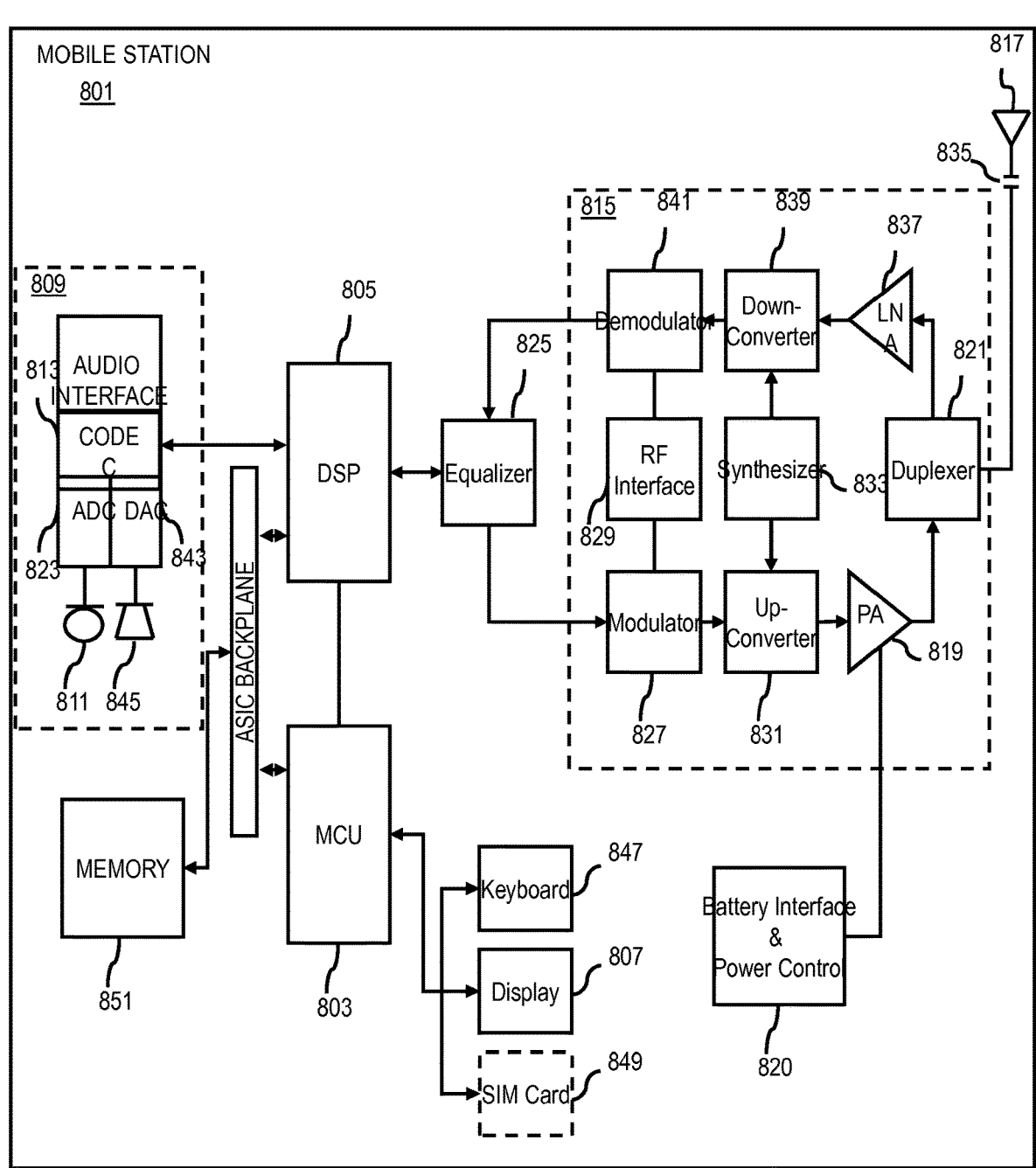
FIG. 8 is a diagram of a mobile terminal (e.g., handset) that can be used to implement an embodiment of the invention.

FIG. 4 is a flowchart that illustrates an example process 400 for the analyzing unit (analyzer 120) of FIG. 1A, according to one embodiment. In one embodiment, the analyzer 120 performs the process 400 and is implemented in, for instance, a chip set including a processor and a memory as shown in FIG. 7 or a general purpose computer as shown in FIG. 6 or mobile terminal as depicted in FIG. 8. In step 401 the signals transmitted from the chip set 220 are received. For example, the digital data indicating the noise reduced, band passed, amplified analog signals are received. In some embodiments, the two analog signals are received and those are common mode noise reduced by differential amplifier and band passed and amplified and digitized in step 401.

In step 403, the digital signal time series is divided into two or more frequency bands corresponding to one or more of the brain wave frequency bands. For example, in some embodiments the digital series is passed through two or more pass bands; or the power density in two or more bands is determined using digital Fourier analysis, such as with a digital Fast Fourier Transform (FFT) well known in the art. For example, in one embodiment, the strength of the beta brain wave band is represented by the power determined for a frequency band from 13 to 19 Hz. Similarly, the strength of the theta brain wave band is represented by the power determined for a frequency band from 4 to 7 Hz.

In step 405 a score is based on the strength or peak frequency of the target band. For example, a score is determined based on the total power density in the two bands, or the ratio of either, or the sum, to a different band, such as the alpha band represented by power density in the frequency band from 8 to 12 Hz, or the frequency of a strongest peak in a brain wave frequency band, in various embodiments. For example, in the experimental embodiment described above, if the subject was focusing, and the beta values were in the desired range (peak amplitude between 14-20 Hz), and the theta activity was in the desired range (a peak amplitude between 4-7 Hz), obstacle bars on the game would become smaller, enabling a little vehicle on the screen to travel along a road on the screen. The more the subject focused and demonstrated a peak value approaching a value of 6 Hz in the target theta band and a value of 17 Hz in the target beta band, the vehicle travelled at the same speed but with fewer obstacles on the road. Furthermore, if the desired ideal state maintained itself because of the subject's focus, for more than 5 seconds continuum, the vehicle would acquire glow, which is an operant conditioning reinforcer, a positive response of the program to the subject, letting the subject know that this is the desired mind state.

In step 407, a magnitude of a stimulus to be presented to the subject is determined based on the score. For example, for a score over a particular threshold value, a game playing subject 190 is rewarded with a treasure or superpower. In step 409, the stimulus determined in step 407 is caused to be presented to the subject, e.g., by sending to the user interface module 132. In some embodiments, step 407 and 409 are performed by the interface server 134.

In step 411, data indicating the subject, time, score or magnitude of the stimulus, or some combination, is sent to the web server 142 for remote access by other users, such as a therapist using web chant 144.

Thus, step 401 includes receiving wirelessly data that indicates an analog signal temporal trace based on a first electroencephalogram potential temporal trace of a subject and a different second electroencephalogram potential temporal trace of the subject. Step 403 includes determining, based on the data, at least a first frequency band and a different second frequency band selected from a group comprising an alpha brain wave band, a beta brain wave band, a delta brain wave band and a theta brain wave band. Step 405 includes determining a score based on a strength of the first frequency band and a strength of the second frequency band. Sending the score to the interface server is one way of causing a stimulus to be presented to the subject based at least in part on the score, as occurs in steps 407 and 409 at the interface server 134 in some embodiments.

By sending data that indicates the subject, time, score, or the magnitude of the stimulus, or some combination to web server 142, step 411 includes causing the signal analyzing unit 120 to cause data that indicates the subject and the score to be made available to a client host 144.

FIG. 5 is a flowchart that illustrates an example process 500 for the web server 142 of FIG. 1A, according to one embodiment. In one embodiment, the web server 142 performs the process 500 and is implemented in, for instance, a general purpose computer as shown in FIG. 6.

In step 501, the web server 142 receives and stores data that indicates the subject, the time, the score or the magnitude of the stimulus, or some combination. In step 503, one or more statistics of subject training are derived based on the sent data, such as percent improvement in attention, or correlation of percent change with the magnitude of the stimulus, or time of day, or elapsed time since powering up the headset 110.

In step 505 it is determined if a request message is received from an authorized user, such as a therapist of the subject. If not, control passes back to step 501 to receive and store more data. If a request message is received, then in step 507 the user is authenticated, if not already authenticated, and an answer for the request is determined and sent to the web client 144 operated by the authorized user, such as the therapist.

The processes described herein for attention training may be advantageously implemented via software, hardware, firmware or a combination of software and/or firmware and/or hardware. For example, the processes described herein, may be advantageously implemented via processor(s), Digital Signal Processing (DSP) chip, an Application Specific Integrated Circuit (ASIC), Field Programmable Gate Arrays (FPGAs), etc. Such exemplary hardware for performing the described functions is detailed below.

FIG. 6 illustrates a computer system 600 upon which an embodiment of the invention may be implemented. Although computer system 600 is depicted with respect to a particular device or equipment, it is contemplated that other devices or equipment (e.g., network elements, servers, etc.) within FIG. 6 can deploy the illustrated hardware and components of system 600. Computer system 600 is programmed (e.g., via computer program code or instructions) as described herein and includes a communication mechanism such as a bus 610 for passing information between other internal and external components of the computer system 600. Information (also called data) is represented as a physical expression of a measurable phenomenon, typically electric voltages, but including, in other embodiments, such phenomena as magnetic, electromagnetic, pressure, chemical, biological, molecular, atomic, sub-atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 600, or a portion thereof, constitutes a means for performing one or more steps as described herein.

A bus 610 includes one or more parallel conductors of information so that information is transferred quickly among devices coupled to the bus 610. One or more processors 602 for processing information are coupled with the bus 610.

A processor (or multiple processors) 602 performs a set of operations on information as specified by computer program code related as described herein. The computer program code is a set of instructions or statements providing instructions for the operation of the processor and/or the computer system to perform specified functions. The code, for example, may be written in a computer programming language that is compiled into a native instruction set of the processor. The code may also be written directly using the native instruction set (e.g., machine language). The set of operations include bringing information in from the bus 610 and placing information on the bus 610. The set of operations also typically include comparing two or more units of information, shifting positions of units of information, and combining two or more units of information, such as by addition or multiplication or logical operations like OR, exclusive OR (XOR), and AND. Each operation of the set of operations that can be performed by the processor is represented to the processor by information called instructions, such as an operation code of one or more digits. A sequence of operations to be executed by the processor 602, such as a sequence of operation codes, constitute processor instructions, also called computer system instructions or, simply, computer instructions. Processors may be implemented as mechanical, electrical, magnetic, optical, chemical or quantum components, among others, alone or in combination.

Computer system 600 also includes a memory 604 coupled to bus 610. The memory 604 such as a random access memory (RAM) or any other dynamic storage device, stores information including processor instructions for steps as described herein. Dynamic memory allows information stored therein to be changed by the computer system 600. RAM allows a unit of information stored at a location called a memory address to be stored and retrieved independently of information at neighboring addresses. The memory 604 is also used by the processor 602 to store temporary values during execution of processor instructions. The computer system 600 also includes a read only memory (ROM) 606 or any other static storage device coupled to the bus 610 for storing static information, including instructions, that is not changed by the computer system 600. Some memory is composed of volatile storage that loses the information stored thereon when power is lost. Also coupled to bus 610 is a non-volatile (persistent) storage device 608, such as a magnetic disk, optical disk or flash card, for storing information, including instructions, that persists even when the computer system 600 is turned off or otherwise loses power.

Information, including instructions for steps as described herein, is provided to the bus 610 for use by the processor from an external input device 612, such as a keyboard containing alphanumeric keys operated by a human user, or a sensor. A sensor detects conditions in its vicinity and transforms those detections into physical expression compatible with the measurable phenomenon used to represent information in computer system 600. Other external devices coupled to bus 610, used primarily for interacting with humans, include a display device 614, such as a cathode ray tube (CRT), a liquid crystal display (LCD), a light emitting diode (LED) display, an organic LED (OLED) display, a plasma screen, or a printer for presenting text or images, and a pointing device 616, such as a mouse, a trackball, cursor direction keys, or a motion sensor, for controlling a position of a small cursor image presented on the display 614 and issuing commands associated with graphical elements presented on the display 614. In some embodiments, for example, in embodiments in which the computer system 600 performs all functions automatically without human input, one or more of external input device 612, display device 614 and pointing device 616 is omitted.

In the illustrated embodiment, special purpose hardware, such as an application specific integrated circuit (ASIC) 620, is coupled to bus 610. The special purpose hardware is configured to perform operations not performed by processor 602 quickly enough for special purposes. Examples of ASICs include graphics accelerator cards for generating images for display 614, cryptographic boards for encrypting and decrypting messages sent over a network, speech recognition, and interfaces to special external devices, such as robotic arms and medic-al scanning equipment that repeatedly perform some complex sequence of operations that are more efficiently implemented in hardware.

Computer system 600 also includes one or more instances of a communications interface 670 coupled to bus 610. Communication interface 670 provides a one-way or two-way communication coupling to a variety of external devices that operate with their own processors, such as printers, scanners and external disks. In general the coupling is with a network link 678 that is connected to a local network 680 to which a variety of external devices with their own processors are connected. For example, communication interface 670 may be a parallel port or a serial port or a universal serial bus (USB) port on a personal computer. In some embodiments, communications interface 670 is an integrated services digital network (ISDN) card or a digital subscriber line (DSL) card or a telephone modern that provides an information communication connection to a corresponding type of telephone line. In some embodiments, a communication interface 670 is a cable modem that converts signals on bus 610 into signals for a communication connection over a coaxial cable or into optical signals for a communication connection over a fiber optic cable. As another example, communications interface 670 may be a local area network (LAN) card to provide a data communication connection to a compatible LAN, such as Ethernet. Wireless links may also be implemented. For wireless links, the communications interface 670 sends or receives or both sends and receives electrical, acoustic or electromagnetic signals, including infrared and optical signals, that carry information streams, such as digital data. For example, in wireless handheld devices, such as mobile telephones like cell phones, the communications interface 670 includes a radio band electromagnetic transmitter and receiver called a radio transceiver. In certain embodiments, the communications interface 670 enables connection to the communication network 105 for one or more steps as described herein to the UE 101.

The term "computer-readable medium" as used herein refers to any medium that participates in providing information to processor 602, including instructions for execution. Such a medium may take many forms, including, but not limited to computer-readable storage medium (e.g., non-volatile media, volatile media), and transmission media. Non-transitory media, such as non-volatile media, include, for example, optical or magnetic disks, such as storage device 608. Volatile media include, for example, dynamic memory 604. Transmission media include, for example, twisted pair cables, coaxial cables, copper wire, fiber optic cables, and carrier waves that travel through space without wires or cables, such as acoustic waves and electromagnetic waves, including radio, optical and infrared waves. Signals include man-made transient variations in amplitude, frequency, phase, polarization or other physical properties transmitted through the transmission media. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, an EPROM, a FLASH-EPROM, an EEPROM, a flash memory, any other memory chip or cartridge, a carrier wave, or any other medium from which a computer can read. The term computer-readable storage medium is used herein to refer to any computer-readable medium except transmission media.

Logic encoded in one or more tangible media includes one or both of processor instructions on a computer-readable storage media and special purpose hardware, such as ASIC 620.

Network link 678 typically provides information communication using transmission media through one or more networks to other devices that use or process the information. For example, network link 678 may provide a connection through local network 680 to a host computer 682 or to equipment 684 operated by an Internet Service Provider (ISP). ISP equipment 684 in turn provides data communication services through the public, world-wide packet-switching communication network of networks now commonly referred to as the Internet 690.

A computer called a server host 692 connected to the Internet hosts a process that provides a service in response to information received over the Internet. For example, server host 692 hosts a process that provides information representing video data for presentation at display 614. It is contemplated that the components of system 600 can be deployed in various configurations within other computer systems, e.g., host 682 and server 692.

At least some embodiments of the invention are related to the use of computer system 600 for implementing some or all of the techniques described herein. According to one embodiment of the invention, those techniques are performed by computer system 600 in response to processor 602 executing one or more sequences of one or more processor instructions contained in memory 604. Such instructions, also called computer instructions, software and program code, may be read into memory 604 from another computer-readable medium such as storage device 608 or network link 678. Execution of the sequences of instructions contained in memory 604 causes processor 602 to perform one or more of the method steps described herein. In alternative embodiments, hardware, such as ASIC 620, may be used in place of or in combination with software to implement the invention. Thus, embodiments of the invention are not limited to any specific combination of hardware and software, unless otherwise explicitly stated herein.

The signals transmitted over network link 678 and other networks through communications interface 670, carry information to and from computer system 600. Computer system 600 can send and receive information, including program code, through the networks 680, 690 among others, through network link 678 and communications interface 670. In an example using the Internet 690, a server host 692 transmits program code for a particular application, requested by a message sent from computer 600, through Internet 690, ISP equipment 684, local network 680 and communications interface 670. The received code may be executed by processor 602 as it is received, or may be stored in memory 604 or in storage device 608 or any other non-volatile storage for later execution, or both. In this manner, computer system 600 may obtain application program code in the form of signals on a carrier wave.

Various forms of computer readable media may be involved in carrying one or more sequence of instructions or data or both to processor 602 for execution. For example, instructions and data may initially be carried on a magnetic disk of a remote computer such as host 682. The remote computer loads the instructions and data into its dynamic memory and sends the instructions and data over a telephone line using a modem. A modem local to the computer system 600 receives the instructions and data on a telephone line and uses an infra-red transmitter to convert the instructions and data to a signal on an infra-red carrier wave serving as the network link 678. An infrared detector serving as communications interface 670 receives the instructions and data carried in the infrared signal and places information representing the instructions and data onto bus 610. Bus 610 carries the information to memory 604 from which processor 602 retrieves and executes the instructions using some of the data sent with the instructions. The instructions and data received in memory 604 may optionally be stored on storage device 608, either before or after execution by the processor 602.

FIG. 7 illustrates a chip set or chip 700 upon which an embodiment of the invention may be implemented. Chip set 700 is programmed to perform one or more steps as described herein and includes, for instance, the processor and memory components described with respect to FIG. 6 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set 700 can be implemented in a single chip. It is further contemplated that in certain embodiments the chip set or chip 700 can be implemented as a single "system on a chip." It is further contemplated that in certain embodiments a separate ASIC would not be used, for example, and that all relevant functions as disclosed herein would be performed by a processor or processors. Chip set or chip 700, or a portion thereof, constitutes a means for performing one or more steps of providing user interface navigation information associated with the availability of functions. Chip set or chip 700, or a portion thereof, constitutes a means for performing one or more steps as described herein.

In one embodiment, the chip set or chip 700 includes a communication mechanism such as a bus 701 for passing information among the components of the chip set 700. A processor 703 has connectivity to the bus 701 to execute instructions and process information stored in, for example, a memory 705. The processor 703 may include one or more processing cores with each core configured to perform independently. A multi-core processor enables multiprocessing within a single physical package. Examples of a multi-core processor include two, four, eight, or greater numbers of processing cores. Alternatively or in addition, the processor 703 may include one or more microprocessors configured in tandem via the bus 701 to enable independent execution of instructions, pipelining, and multithreading. The processor 703 may also be accompanied with one or more specialized components to perform certain processing functions and tasks such as one or more digital signal processors (DSP) 707, or one or more application-specific integrated circuits (ASIC) 709. A DSP 707 typically is configured to process real-world signals (e.g., sound) in real time independently of the processor 703. Similarly, an ASIC 709 can be configured to performed specialized functions not easily performed by a more general purpose processor. Other specialized components to aid in performing the inventive functions described herein may include one or more field programmable gate arrays (FPGA) (not shown), one or more controllers (not shown), or one or more other special-purpose computer chips.

In one embodiment, the chip set or chip 700 includes merely one or more processors and some software and/or firmware supporting and/or relating to and/or for the one or more processors.

The processor 703 and accompanying components have connectivity to the memory 705 via the bus 701. The memory 705 includes both dynamic memory (e.g., RAM, magnetic disk, writable optical disk, etc.) and static memory (e.g., ROM, CD-ROM, etc.) for storing executable instructions that when executed perform the inventive steps described herein. The memory 705 also stores the data associated with or generated by the execution of the inventive steps.

FIG. 8 is a diagram of exemplary components of a mobile terminal (e.g., handset) for communications, which is capable of operating in the system of FIG. 1, according to one embodiment. In some embodiments, mobile terminal 801 or a portion thereof, constitutes a means for performing one or more steps described herein. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a base-band integrated circuit or applications processor integrated circuit in a mobile phone or a similar integrated circuit in a cellular network device or other network deices.

Pertinent internal components of the telephone include a Main Control Unit (MCU) 803, a Digital Signal Processor (DSP) 805, and a receiver/transmitter unit including a microphone gain control unit and a speaker gain control unit. A main display unit 807 provides a display to the user in support of various applications and mobile terminal functions that perform or support the steps as described herein. The display 807 includes display circuitry configured to display at least a portion of a user interface of the mobile terminal (e.g., mobile telephone). Additionally, the display 807 and display circuitry are configured to facilitate user control of at least some functions of the mobile terminal. An audio function circuitry 809 includes a microphone 811 and microphone amplifier that amplifies the speech signal output from the microphone 811. The amplified speech signal output from the microphone 811 is fed to a coder/decoder (CODEC) 813.

A radio section 815 amplifies power and converts frequency in order to communicate with a base station, which is included in a mobile communication system, via antenna 817. The power amplifier (PA) 819 and the transmitter/modulation circuitry are operationally responsive to the MCU 803, with an output from the PA 819 coupled to the duplexer 821 or circulator or antenna switch, as known in the art. The PA 819 also couples to a battery interface and power control unit 820.

In use, a user of mobile terminal 801 speaks into the microphone 811 and his or her voice along with any detected background noise is converted into an analog voltage. The analog voltage is then converted into a digital signal through the Analog to Digital Converter (ADC) 823. The control unit 803 routes the digital signal into the DSP 805 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 825 for compensation of any frequency-dependent impairments that occur during transmission though the air such as phase and amplitude distortion. After equalizing the bit stream, the modulator 827 combines the signal with a RF signal generated in the RF interface 829. The modulator 827 generates a sine wave by way of frequency or phase modulation. In order to prepare the signal for transmission, an up-converter 831 combines the sine wave output from the modulator 827 with another sine wave generated by a synthesizer 833 to achieve the desired frequency of transmission. The signal is then sent through a PA 819 to increase the signal to an appropriate power level. In practical systems, the PA 819 acts as a variable gain amplifier whose gain is controlled by the DSP 805 from information received from a network base station. The signal is then filtered within the duplexer 821 and optionally sent to an antenna coupler 835 to match impedances to provide maximum power transfer. Finally, the signal is transmitted via antenna 817 to a local base station. An automatic gain control (AGC) can be supplied to control the gain of the final stages of the receiver. The signals may be forwarded from there to a remote telephone which may be another cellular telephone, any other mobile phone or a land-line connected to a Public Switched Telephone Network (PSTN), or other telephony networks.

Voice signals transmitted to the mobile terminal 801 are received via antenna 817 and immediately amplified by a low noise amplifier (LNA) 837. A down-converter 839 lowers the carrier frequency while the demodulator 841 strips away the RF leaving only a digital bit stream. The signal then goes through the equalizer 825 and is processed by the DSP 805. A Digital to Analog Converter (DAC) 843 converts the signal and the resulting output is transmitted to the user through the speaker 845, all under control of a Main Control Unit (MCU) 803 which can be implemented as a Central Processing Unit (CPU) (not shown).

The MCU 803 receives various signals including input signals from the keyboard 847. The keyboard 847 and/or the MCU 803 in combination with other user input components (e.g., the microphone 811) comprise a user interface circuitry for managing user input. The MCU 803 runs a user interface software to facilitate user control of at least some functions of the mobile terminal 801 as described herein. The MCU 803 also delivers a display command and a switch command to the display 807 and to the speech output switching controller, respectively. Further, the MCU 803 exchanges information with the DSP 805 and can access an optionally incorporated SIM card 849 and a memory 851. In addition, the MCU 803 executes various control functions required of the terminal. The DSP 805 may, depending upon the implementation, perform any of a variety of conventional digital processing functions on the voice signals. Additionally, DSP 805 determines the background noise level of the local environment from the signals detected by microphone 811 and sets the gain of microphone 811 to a level selected to compensate for the natural tendency of the user of the mobile terminal 801.

The CODEC 813 includes the ADC 823 and DAC 843. The memory 851 stores various data including call incoming tone data and is capable of storing other data including music data received via, e.g., the global Internet. The software module could reside in RAM memory, flash memory, registers, or any other form of writable storage medium known in the art. The memory device 851 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 849 carries, for instance, important information, such as the cellular phone number, the carrier supplying service, subscription details, and security information. The SIM card 849 serves primarily to identify the mobile terminal 801 on a radio network. The card 849 also contains a memory for storing a personal telephone number registry, text messages, and user specific mobile terminal settings.

While the invention has been described in connection with a number of embodiments and implementations, the invention is not so limited but covers various obvious modifications and equivalent arrangements, which fall within the purview of the appended claims. Although features of the invention are expressed in certain combinations among the claims, it is contemplated that these features can be arranged in any combination and order.

The invention claimed is:

1. A system comprising:
 a headband configured to fit to a head of a subject;
 at least three active electrodes coupled to the headband, wherein
  a first electrode comprises a first hemispherical metal coated core positioned to contact the head of the subject at a first position;
  a second electrode comprises a second hemispherical metal coated core positioned to contact the head of the subject at a second position; and
  a third electrode is positioned at a third position;
 a chipset configured to determine an analog signal based at least in part on a first signal received from the first electrode and a second signal received from the second electrode and transmit digital data that indicates the analog signal; and
 at least one computing device comprising:
  at least one processor; and
  at least one memory embodying a set of executable instructions that, when executed, cause the at least one processor to at least:
   determine, based at least in part on the digital data, at least a first frequency band, the first frequency band comprising one of: an alpha brain wave band, a beta brain wave band, a delta brain wave band or a theta brain wave band;
   determine, based at least in part on the digital data, a different second frequency band comprising one of: an alpha brain wave band, a beta brain wave band, a delta brain wave band or a theta brain wave band;
   determine a score based at least in part on the first frequency band and a strength or peak frequency of the different second frequency band relative to the first frequency band; and
   cause a stimulus to be presented to the subject based at least in part on the score.

2. The system of claim 1, wherein the set of executable instructions of the at least one computing device further cause the at least one processor to cause data that indicates the subject and the score to be made available to a client host.

3. The system of claim 1, wherein the first position corresponding to about a Cz location on the subject according to a 10-20 electrode placement system of an International Federation of Electroencephalography and Clinical Neurophysiology, the second position corresponding to about a first mastoid location on the subject, and the third position corresponding to about a second mastoid location on a side of the head of the subject opposite the first mastoid location.

4. The system of claim 1, wherein the first electrode and the second electrode are copper coated beryllium copper core electrodes that make electrical contact with the head of the subject with an electrical impedance of less than about 3 kilo ohms.

5. The system of claim 1, wherein the chipset comprises a plurality of graphene conductors.

6. The system of claim 1, wherein the analog signal indicates a common mode noise reduced difference between the first signal and the second signal in a frequency band from about four (4) Hertz to about twenty (20) Hertz, comprising beta brain waves, alpha brain waves, and theta brain waves.

7. The system of claim 1, wherein the analog signal indicates a common mode noise reduced difference between the first signal and the second signal in a frequency band from about one quarter (0.25) Hertz to about forty (40) Hertz, comprising alpha brain waves, beta brain waves, delta brain waves and theta brain waves.

8. The system of claim 1, wherein a contact of the first hemispherical metal coated core and the second hemispherical metal coated core with the head of the subject is a non-liquid contact providing an electrical contact for pre-processing and wireless transmission of data.

9. The system of claim 8, wherein causing the at least one processor to at least determine a score based at least in part on the first frequency band and the different second frequency band further causes the at least one to at least determine the score based at least in part on a strength or peak frequency of the first frequency band and a strength or peak frequency of the different second frequency band.

10. The system of claim 9, wherein the set of executable instructions further cause the at least one processor of the at least one computing device to determine, based at least in part on the digital data, a third frequency band selected from a group consisting of an alpha brain wave band, a beta brain wave band, a delta brain wave band and a theta brain wave band, the third frequency band different than the first frequency band and second frequency band.

11. The system of claim 10, wherein the set of executable instructions further cause the at least one processor of the at least one computing device to determine, based at least in part on the digital data, a fourth frequency band selected from a group consisting of an alpha brain wave band, a beta brain wave band, a delta brain wave band and a theta brain wave band, the fourth frequency band different than the first frequency band, the second frequency band, and the third frequency band.

12. The system of claim 1, wherein the set of executable instructions further cause the at least one processor of the at least one computing device to determine a magnitude of stimulus to present based at least in part on the score.

13. The system of claim 1, wherein the set of executable instructions further cause the at least one processor of the at least one computing device to transmit transmitted data to a server following presentation of the stimulus to the subject.

14. The system of claim 13, wherein the transmitted data comprises subject data, time data, relative strength of target data, and magnitude of stimulus data.

15. The system of claim 1, wherein the first hemispherical metal coated core comprises a radius of about three millimeters or less extending perpendicular to the headband by a distance about equal to the radius of the first hemispherical metal coated core, the first hemispherical metal coated core.

16. The system of claim 1, further comprising a client host, wherein the client host comprises:

at least one client host processor; and at least one client host memory comprising executable instructions that, when executed, cause the at least one processor to at least:

transmit a request message for data corresponding to the subject to the at least one computing device;

in response to transmitting the request message, receiving first data that indicates the subject and the score; and presenting, to a user, second data that indicates the subject and the score.

17. The system of claim 1, wherein at least one of the first electrode, the second electrode, or the third electrode are disposed in the headband.

18. The system of claim 1, wherein the digital data is transmitted using a wireless communication protocol.

19. The system of claim 1, further comprising a user interface module.

20. The system of claim 1, wherein the first electrode and the second electrode include a core of a beryllium copper alloy, the beryllium copper alloy comprising:

more than three percent by weight beryllium;

less than three percent other metals; and a substantively remaining percent by weight copper.

* * * * *